United States Patent
Lu et al.

(10) Patent No.: US 7,120,484 B2
(45) Date of Patent: Oct. 10, 2006

(54) METHODS AND APPARATUS FOR FILTERING EGM SIGNALS DETECTED BY AN IMPLANTABLE MEDICAL DEVICE

(75) Inventors: Steven N. Lu, Fridley, MN (US);
Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 626 days.

(21) Appl. No.: 10/045,722

(22) Filed: Jan. 14, 2002

(65) Prior Publication Data

US 2003/0135125 A1     Jul. 17, 2003

(51) Int. Cl.
*A61B 5/04* (2006.01)
(52) U.S. Cl. .................................................. 600/515
(58) Field of Classification Search ................ 600/513, 600/510, 515
See application file for complete search history.

(56) References Cited

U.S. PATENT DOCUMENTS

| | | | |
|---|---|---|---|
| 5,297,557 A | 3/1994 | Reichl | 128/707 |
| 5,331,966 A | 7/1994 | Bennett et al. | 128/696 |
| 5,402,795 A | 4/1995 | Reichl | 128/696 |
| 5,479,922 A | 1/1996 | Reichl | 128/630 |
| 5,544,661 A | 8/1996 | Davis et al. | 128/700 |
| 5,564,434 A | 10/1996 | Halperin et al. | 128/748 |
| 5,626,620 A | 5/1997 | Kieval et al. | 607/9 |
| 5,683,432 A | 11/1997 | Goedeke et al. | 607/32 |
| 5,772,603 A | 6/1998 | Ohlsson et al. | 600/509 |
| 5,843,139 A | 12/1998 | Goedeke et al. | 607/32 |
| 5,931,857 A | 8/1999 | Prieve et al. | 607/14 |
| 5,954,660 A | 9/1999 | Legay et al. | 600/509 |
| 5,997,476 A | 12/1999 | Brown | 600/300 |
| 6,128,526 A | 10/2000 | Stadler et al. | 600/517 |
| 6,221,011 B1 | 4/2001 | Bardy | 600/300 |
| 6,317,625 B1 | 11/2001 | Olson et al. | 600/509 |

FOREIGN PATENT DOCUMENTS

| | | |
|---|---|---|
| EP | 1 057 448 A1 | 12/2000 |
| WO | WO 98/02209 | 1/1998 |
| WO | WO 99/41682 | 3/1999 |
| WO | WO 99/14882 | 8/1999 |
| WO | WO 00/70529 | 11/2000 |

*Primary Examiner*—Mark Bockelman
(74) *Attorney, Agent, or Firm*—Paul H. McDowall; Girma Wolde-Michael

(57) ABSTRACT

An analog physiologic signal, e.g., the cardiac EGM, sensed by an IMD is filtered with a high pass filter (HPF), the cut-off frequency of the HPF being within a predetermined frequency bandwidth, wherein a low-band portion of the predetermined frequency bandwidth is attenuated in the filtered physiologic signal. The filtered physiologic signal is digitized in real time order, and the digital data set is filtered in reverse time order employing a digital IIR filter having characteristics substantially matching the cut-off frequency and filter characteristics of the HPF. When the system is implemented within an IMD, the filtered digital data set is compressed by lossy compression algorithm, and the compressed data set is filtered in reverse time order. In certain embodiments, the filtered digital data set is uplink telemetry transmitted to an external medical device, and the uplink telemetered data set is filtered in reverse time order employing a digital backward IIR filter resident in the external medical device.

21 Claims, 3 Drawing Sheets

METHODS AND APPARATUS FOR FILTERING EGM SIGNALS DETECTED BY AN IMPLANTABLE MEDICAL DEVICE

FIELD OF THE INVENTION

The present invention relates generally to the field of implantable medical devices (IMDs), and more particularly to methods and apparatus for filtering signals detected by an IMD.

BACKGROUND OF THE INVENTION

The electrocardiogram (ECG) or electrogram (EGM) of the cardiac cycle detected across sense electrode pairs located on the patient's skin or in the patient's body, respectively, is a repetitive waveform characterized by a periodic PQRST electrical activation sequence of the upper and lower heart chambers. The PQRST sequence is associated with the sequential depolarization and contraction of the atria followed by the depolarization and contraction of the ventricles, and successive PQRST complexes are separated by a baseline or isoelectric region. The PQRST electrical activation sequence commences with the P-wave indicative of the depolarization and contraction of the atria and is followed by the QRS complex indicative of the depolarization and contraction of the ventricles. The T-wave at the termination of the ST segment time delay is associated with repolarization of the ventricles. The PQRST electrical activation sequence with intact A-V activation detected across a sense electrode pair is fairly predictable in shape. The P-wave, R-wave and T-wave events occurring in sequence in the range of normal heart rates are usually readily recognized by visual examination of the external ECG or an EGM recorded by implanted electrodes that are correctly oriented with the depolarization waves. The P-wave and R-wave are readily sensed by sense amplifiers of a monitor or therapy delivery device coupled with appropriately placed sense electrode pairs.

The ECG and EGM signals are often plagued by baseline wander involving large amplitude, low-frequency, non-physiological signals that, in the IMD context, can saturate a measurement system, resulting in the loss of signal fidelity. Sources of baseline wander include patient movement that disturb the electrode-tissue interface, causing a low frequency signal to be superimposed on the EGM, and voltage after-potentials that linger in the electrode-tissue interface following delivery of pacing or cardioversion energy through the electrodes. The fidelity of recording, displaying, and analyzing ECGs is reduced by such noise. Also, in most current IMDs, the analog EGM is applied to an analog-to-digital converter (ADC) so that the encoded data can be stored in IMD memory and/or uplink telemetry transmitted. Baseline wander increases the dynamic range of the EGM signal such that higher bit resolution and higher dynamic range or the ADC are needed to digitize the analog EGM. The consumption of current from the IMD battery undesirably increases as ADC bit resolution and dynamic range are increased.

Due to the above-mentioned problems, the ECG and EGM signals must be bandpass filtered to block such noise without itself reducing ECG and EGM signal quality. The sense amplifiers of external ECG equipment are normally employed with skin electrodes applied to the patient's skin, and the ECG signals are often plagued by interference from stochastic or random noise or by 50 Hz or 60 Hz electrical mains noise in the patient's body. The fidelity of recording, displaying, and analyzing ECGs is reduced by such noise. Therefore, the ECG signals must be bandpass filtered to block such noise without itself reducing ECG signal quality. The high pass filter cut-off frequency must be selected to still enable passage of the low frequency components of the ECG, e.g., any baseline deviations due to ST segment elevation or depression caused by cardiac ischemia.

The Ad Hoc Writing Group of the Committee on Electrocardiography and Cardiac Electrophysiology of the Council on Clinical Cardiology of the American Heart Association and the Association for the Advancement of Medical Instrumentation (AAMI) recommend that the low frequency cut-off should be on the order of 0.67 Hz provided that the filter meets certain phase and amplitude requirements. Although these recommendations were written specifically for surface ECG instruments and similar documents for intracardiac electrogram instruments do not exist, they provide general guidelines for improving the value and performance of IMD based EGM recording to observe ischemia. The AAMI standards require recording instruments to reproduce a 3 mV by 100 ms step input with no more than a 100 µV overshoot. Any first order RC high pass filter with corner frequency at or below 0.05 Hz and any linear-phase high pass filter with corner frequency at or below 0.67 Hz will pass this step input test. Both of these implementations can be found in today's commercial surface ECG instruments.

Various techniques have been employed to reduce baseline distortion in ECG signals. The most common technique presently used is Cubic-Spline interpolation where the onset of QRS signals are isolated and interpolation techniques are employed to determine the smoothest curve joining several QRS onsets. The ECG baseline can then be estimated by subtracting the curve representing the baseline wander as estimated by the Cubic-Spline technique from the recorded ECG signal. However, the QRS onset points used by the Cubic-Spline method, do not sufficiently model noise in an ECG baseline due to the scarcity of interpolation points at low heart rates. Determination of the QRS onset can be difficult or impossible in the presence of high amplitude baseline wander. Furthermore, it is necessary to delay the ECG in order to obtain reference points (QRS onset points) for calculation of the Cubic-Spline curve. This delay (often as long as 5 seconds or longer) renders the Cubic-Spline interpolation unsuitable for real time monitoring of patients.

A faster method of correcting baseline distortion has been to use high pass filtering techniques. One such filtering technique is to employ Finite Impulse Response (FIR) filters as suggested in U.S. Pat. No. 5,772,603, for example. In one approach, the output is taken after the FIR transfer is combined with a delay based on an integral number of the filter. These filters offer a linear phase response providing an undistorted ECG signal. FIR filters have the disadvantage of being highly computational. Nearly ideal filter characteristics may be obtained at the price of having to perform many floating point calculations and additions.

A commonly used FIR filter is the Comb Filter which is a recursive implementation of a non-recursive FIR filter. While offering the advantage of significantly lower computational requirements, this filter offers only moderate attenuation of baseline noise. The maximum stop band attenuation of the Comb Filter is a modest −13.5 db. Another disadvantage of this type of filter is that it has a wide pass band to stop band transition in the frequency domain resulting in poor noise attenuation near the cut-off frequency.

It has also been proposed to employ high pass Infinite Impulse Response (IIR) filters which are recursive filters that offer the advantage of fewer computations than FIR filters. However, the nonlinear phase response of high pass IIR filters causes an unacceptable level of phase distortion of the ECG signal. The nonlinear phase response causes different frequency components of the signal to be delayed or shifted in time by different degrees. The worst distortion occurs at of just above the cut-off frequency of the filter for the class of filters appropriate to ECG filtering, that is, Butterworth filters that have maximally flat frequency response.

A solution to the phase distortion problem is to apply the ECG signal in a forward direction, which can be in real time, and then in a backward or reverse directions to the IIR filter, which is referred to as a "zero phase IIR filter". The ECG baseline distortions are filtered out when the ECG passes through the zero phase IIR filter in the forward direction, but the ECG signal itself is distorted. The reverse direction filtering process corrects the distortion of the ECG signal and further attenuates baseline noise.

The use of such a zero phase IIR filter effective in achieving 0.67 Hz passband frequencies on ECG signals is disclosed in U.S. Pat. Nos. 5,297,557, 5,402,795, and 5,479,922 wherein the ECG signal is filtered in the forward direction over a selected window, and then the same window is filtered in a reverse direction to remove phase distortion. It is asserted that the delays associated with use of the zero phase IIR filter in this manner are small enough to enable real time ECG measurement and display of patients engaged in stress exercise. Two basic filter variations are disclosed that are implementations of analog 3 pole or 5 pole Butterworth filters that offer a trade-off between computational complexity, stop band attenuation, phase response and transient settling time. Other filters, such as Bessel filters, may be used in place of the design employing the Butterworth filter. The Bessel filter has the advantage of providing a design containing less overshoot in response to impulse signals and the disadvantage of providing less attenuation in the stop band.

As already mentioned, in most current IMDs, the analog EGM is applied to an analog-to-digital converter (ADC) so that the encoded data can be stored in IMD memory and/or uplink telemetry transmitted. Baseline wander increases the dynamic range of the EGM signal such that higher bit resolution and higher dynamic range or the ADC is needed to digitize the analog EGM. The consumption of current from the IMD battery undesirably increases as ADC bit resolution and dynamic range is increased. The previously mentioned methods involving use of the Cubic-Spline interpolation technique, FIR, or the zero-phase IIR filters used in '557, '795, '922 patents are digital signal processing techniques for removing baseline wander. In most of these techniques, the removal of baseline wander can only occur after the EGM to be filtered is digitized. Therefore, these techniques need to be employed with an ADC with higher bit resolution and wider dynamic range.

In commonly assigned U.S. Pat. No. 6,317,625, a signal measuring system for an IMD is provided for sensing EGM signals having a relatively large effective dynamic range due to baseline wander without increasing ADC bit resolution and dynamic range. Low frequency compression/enhancement techniques are combined with dither techniques to effectively increase the dynamic range while maintaining resolution without increasing the number of bits of the ADC that is used to convert the sensed signal to digital format. In one embodiment, the system includes a high-pass filter (HPF), an analog-to-digital converter (ADC), a decimation filter (DF), and a compensation filter (CF). The EGM (including baseline wander imposed on the EGM) is passed through the HPF, and the HPF attenuates the low frequency components of the signal. Unlike conventional systems, the HPF serves to attenuate the bias current signal so that the sampled signal remains within the dynamic range of the system. In one embodiment, the HPF attenuates frequency components that are within the frequency bandwidth of the desired output signal. The ADC then over-samples the output signal of the HPF. The DF receives the output samples of the ADC and generates output samples at a rate that is at least twice the maximum frequency of the desired output signal. The CF then amplifies the low frequency end of the DF output samples. The gain and cut-off frequency of the CF are, ideally, set to substantially offset the attenuation of the HFP for those low frequency components of the input signal below the cut-off frequency of the HPF and above the minimum frequency of the desired output signal. Although it would appear that the resolution of these low frequency components has been degraded, dither techniques are used, in effect, to exchange sample rate for resolution. In one embodiment, system noise (noise inherent in the system due to imperfections in the components, thermal noise, etc.) is used as the dither. As a result of the compression/enhancement and dither techniques, the output signal remains within the dynamic range of the system with the desired resolution, which allows the system to display an accurately measured signal significantly faster than conventional systems.

Thus, the system disclosed in the '625 patent avoids the necessity of increasing the ADC bit resolution so that the EGM can be digitized by an ADC with lower dynamic range and then reconstructs the EGM after it has been digitized. But, the reconstruction process reconstructs both the desired EGM signal and the noise or baseline wander.

Although the above-described methods and apparatus represents a substantial improvement over the prior art, further improvement is, of course, generally desirable. Thus, there is a need for a low-cost, energy-efficient, physiological signal measuring system for use in an IMD having a relatively large dynamic range, high resolution, high fidelity, and good noise rejection characteristics. The system should minimize the changes in the morphology of the physiological signal being measured and minimize the noise content of the signal recorded so that the ability to provide accurate patient diagnoses based on the signal characteristics is not only uncompromised, but is enhanced.

SUMMARY OF THE INVENTION

The present invention follows the discovery of methods and apparatus for measuring and filtering stochastic noise from an EGM signal or other physiologic signal sensed by an IMD wherein the measured physiological signal covers a relatively large dynamic range. In one aspect of the present invention, analog and digital low frequency filtering techniques are used in combination to effectively reduce the dynamic range of the signal while maintaining the morphology of the signal of interest. This aspect of the present invention is achieved without increasing the number of bits of the ADC that is used to convert the sensed signal to digital format.

The methods and apparatus disclosed herein involve a system of obtaining an analog physiological signal from a sensor coupled to the IMD, filtering the analog physiologic signal with a high pass filter (HPF), the cut-off frequency of the HPF being within the predetermined frequency bandwidth, wherein a low-band portion of the predetermined frequency bandwidth is attenuated in the filtered physiologic signal, sampling and digitizing the filtered physiologic signal as a filtered digital data set in real time order, and filtering the compressed data set in reverse time order employing a digital backward IIR filter having characteristics substantially matching the cut-off frequency and filter characteristics of the HPF. The HPF is implemented in hardware, whereas the digital backward IIR filter is implemented in software.

When the system is implemented within an IMD, the filtered digital data set is can be compressed by lossy compression algorithms such as a "peak preserving compression algorithm" to achieve 2:1, 4:1, or even higher data compression rates, and the compressed data set is filtered in reverse time order employing the backward digital IIR filter.

In certain embodiments, the filtered digital data set is uplink telemetry transmitted to an external medical device, and the uplink telemetered data set is filtered in reverse time order employing a digital backward IIR filter resident in the external medical device.

The low frequency filtering techniques used by the present invention allow the morphology of the waveform to be retained. Thus, unlike conventional systems that remove and/or distort important low-frequency components from the waveform, making conditions such as ischemia difficult, if not impossible, to diagnose, the current system generates waveform data that includes important low-frequency information needed to make an accurate diagnosis.

The method and apparatus of the present invention advantageously filters out the baseline wander and noise so the EGM can be digitized employing a low current consuming ADC having normal bit resolution and dynamic range. Then, the distortion caused by the initial filter is removed by the reverse or backward IIR filter to obtain an accurate recording of the EGM without the baseline wander and noise. While the method of the present invention cannot be done in real-time, it is possible to process digitized EGM data streams encompassing one or more a PQRST complex within the time period between successive PQRST complexes to effect a pseudo real-time EGM signal processing method and system.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

The present invention can be implemented in any IMD having the capacity of sensing a physiologic signal and processing the signal in accordance with the present invention either in the IMD or in an external EMD in proximate or remote communication with the IMD employing mutual uplink and downlink telemetry capabilities. At present, a wide variety of IMDs are commercially released or proposed for clinical implantation. Such medical devices include implantable cardiac pacemakers as well as ICDs, pacemaker-cardioverter-defibrillators, drug delivery pumps, cardiomyostimulators, cardiac and other physiologic monitors, nerve and muscle stimulators, deep brain stimulators, cochlear implants, artificial hearts, etc. As the technology advances, IMDs become ever more complex in possible programmable operating modes, menus of available operating parameters, and capabilities of monitoring increasing varieties of physiologic conditions and electrical signals which place ever increasing demands on the signal processing capabilities of the IMD. Such IMDs can also comprise more than one discrete IMD implanted within the same patient that communicate with one another and with an EMD.

However, as noted at the outset, the present invention is particularly suitable for processing the EGM sensed in an IMD to be able to accurately sense, store or transmit the EGM to an EMD with high signal fidelity that eliminates baseline drift, stochastic noise and the like that distort the ST segment. Thus, the present invention has particular application to the processing of the EGM to ensure that ST segment deviations from baseline due to ischemia are accurately depicted when the EGM is reconstituted and displayed for view by a medical care provider or provided for comparison to thresholds or templates for automatic ischemia detection.

Figure 1:
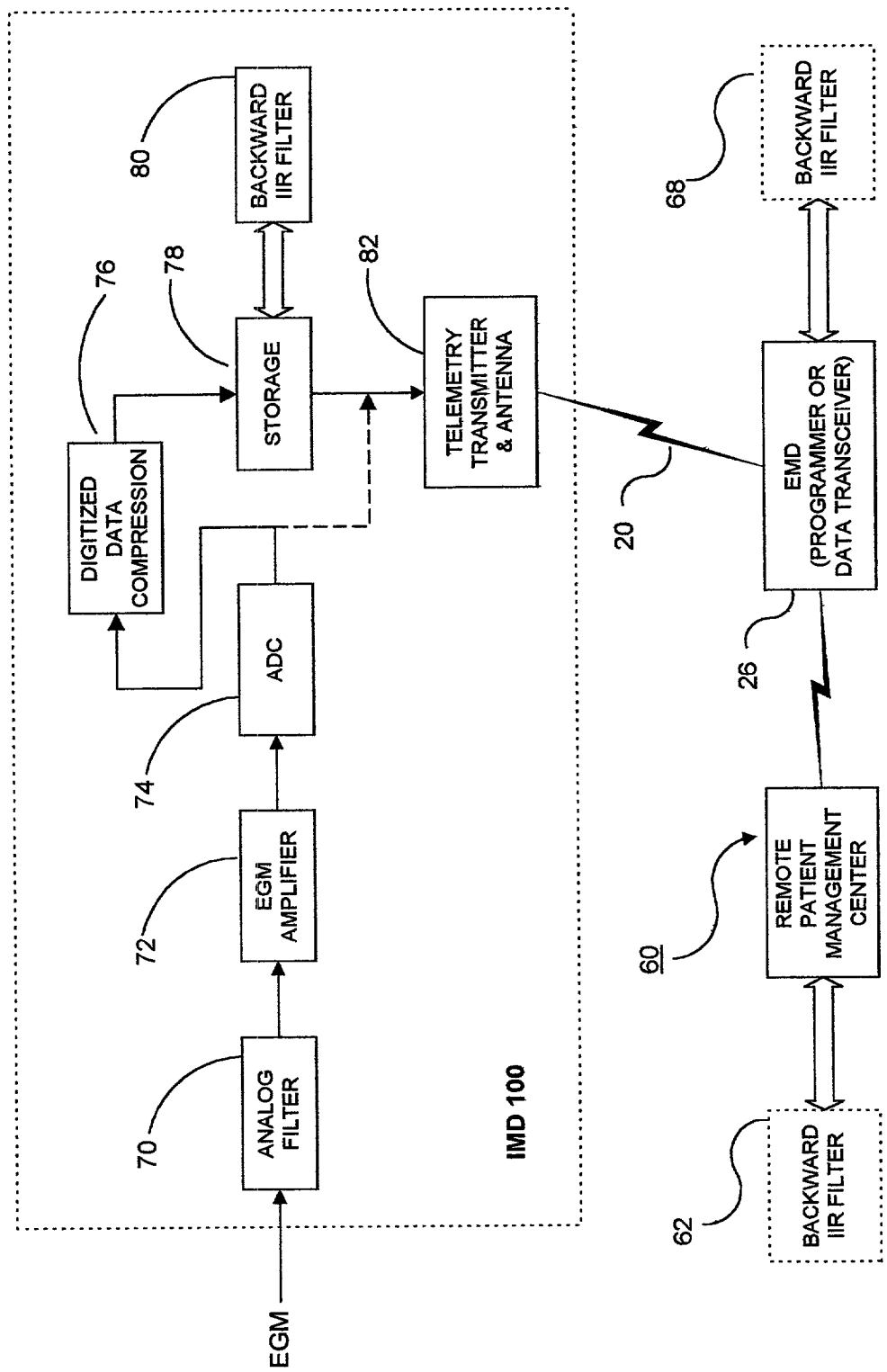
FIG. 1 is a simplified signal processing system providing alternative ways of implementing the present invention in an IMD and an EMD and optionally involving a remote patient management center.

FIG. 1 is a simplified signal processing system providing alternative ways of implementing the present invention in an IMD 100 and an EMD 26 and optionally involving a remote patient management center 60. The IMD 100 includes a high pass analog filter (HPF) 70 that filters the incoming EGM, and the filtered EGM is amplified by the EGM sense amplifier 72 in real time. The HPF 70 may be interposed between a preamplifier (not shown) and the EGM sense amplifier 72. The HPF 70 preferably has a cut-off frequency no higher than 0.67 Hz which satisfies the above-described AHA and AAMI recommendations for ischemia monitoring. However, it can have a higher cut-off frequency, e.g., the above-described 2.5 Hz cut-off frequency if the purpose is other than ischemia monitoring. The HPF 70 is preferably implemented in hardware and can be a first or higher order filter. The filtered and amplified EGM is then sampled and digitized by the ADC 74, and the digitized data stream is either compressed by a compression algorithm 76 to facilitate storage in IMD storage 78 or is stored directly in IMD storage 78 bypassing compression algorithm 76 or is applied to telemetry transmitter and antenna 82 for uplink telemetry transmission to an EMD 26 in real time. For example, the IMD 100 may be commanded to enter an EGM transmission mode by a downlink telemetry transmitted command from EMD 26 or to do so when ischemia event criteria are met or at a particular time of day or when the patient initiates the EGM transmission mode on feeling symptoms of ischemia.

In this embodiment, ADC 74 is implemented using a twelve-bit ADC, such as, for example, a model AD7892 available from Analog Devices, Norwood, Mass., with a 5 kilo samples-per-second (ksps) sampling rate on each of a large number of sequentially selected channels. Those skilled in the art will appreciate that the ADC selected need not be a twelve-bit device and many other ADC devices could be used. For an input signal with a 20 µV dynamic range, twelve-bit ADC 74 will generate a digital output signal with 5 µV resolution (i.e., a uniform 5 µV step size).

In addition, the IMD 100 may initiate the EGM signal processing and storage of digitized EGM data blocks when ischemia event criteria are met or at a particular time of day or when the patient initiates the EGM storage mode on feeling symptoms of ischemia. Alternatively, the EGM may be continuously processed and temporarily stored in storage 78 on a FIFO basis and only stored on a more permanent basis when event criteria are met or at a particular time of day or when the patient initiates the EGM storage mode on feeling symptoms of ischemia.

After a time segment of digitized EGM data is stored in storage 78, the block of data is subjected to reverse or backward IIR filtering by backward IIR filter 80. The backward IIR filter 80 is preferably implemented in software and has characteristics substantially matching the cut-off frequency and filter characteristics of the HPF 70. The backward filtering process filters the stored EGM data in a first-in-last-out manner, thus introducing the same phase-distortion as the analog filter 70 but in a reverse time sequence. This results in the cancellation of phase distortion between the analog and the digital filters.

The time segment can be a programmable time segment that is in the range of several seconds. A short time segment is desirable to minimize the delay of the system and to provide a pseudo real-time output. However, the backward IIR filtering process will generate a start-up transient period where not all the distortions are cancelled. A longer time segment will reduce the amount of start-up transient periods in the overall recording. Time segments of several seconds have been found to be both a tolerable delay and a long enough time segment for proper phase distortion cancellation.

The resulting forward and backward filtered data block is either stored in storage 78 for future uplink telemetry transmission or is subjected to ischemia detection as a function of detected deviation from baseline as described above. Any time segments of digitized EGM data signifying these criteria would then be saved in storage 78 with a date stamp and other pertinent physiologic data.

As noted above, the digitized EGM data stream can be uplink telemetry transmitted to the EMD 26 which can be a programmer or can be a data transceiver in communication with a remote patient management center 60. In this case, the uplink telemetry transmitted EGM data is stored in memory either in the EMD or in the remote patient management center. Blocks of the stored EGM data can then be filtered in reverse time order using the backward IIR filter software of backward IIR filters 62 or 68.

A two-way telemetry session to uplink telemeter the real time or stored EGM data is typically initiated in the presence of a health care provider, that is a treating or implanting physician or a physician's assistant or the like who is technically and medically trained sufficiently to operate the programmer, safely reprogram an operating mode or parameter of the IMD, and initiate uplink telemetry of patient data. Normally, this is done in a clinic, hospital room or physician's office at implant and periodically as deemed advisable during the time that the IMD remains implanted. The patient may have to travel a distance and take time away from employment to participate in the telemetry session. The patient would have to stay under medical care indefinitely if the medical conditions of the patient warrant continuous monitoring of the IMD.

Continuous updating and monitoring of the IMDs is necessary to successfully manage the operations and assess the performance of each IMD in the patient receiving one IMD, much less multiple IMDs and interactions with drug therapies. There is a need to monitor the performance of the IMDs on a regular, if not a continuous, basis to ensure optimal patient care. In the absence of other alternatives, this imposes a great burden on the patient if a hospital or clinic is the only center where the necessary frequent follow up, evaluation and adjustment of the IMDs could be made. Moreover, even if feasible, an increasing number of health care providers and increased numbers of service areas or clinic centers would be required to provide adequate medical care to the burgeoning number of patients implanted with one or more IMD worldwide.

Over the years, many systems have been advanced for remote monitoring of patients through radio or telephone communication or "telemedicine" links as disclosed, for example, in U.S. Pat. No. 5,544,661. More recently, systems for effecting interactive communication and remote monitoring of ambulatory patients have been proposed employing Internet based information technologies as disclosed in U.S. Pat. No. 5,997,476 and in PCT Publication Nos. WO 99/14882 and WO 99/41682, for example. Various systems have been proposed to provide medical information and assistance to patient subscribers to Internet based services as disclosed in PCT Publication No. WO 00/70529, for example.

Thus, a number of proposals have been advanced to facilitate conducting telemetry sessions with IMDs virtually automatically employing information technologies and available networks of the types listed above. Typically, a central database and communications center is manned by a staff that initiates a remote telemetry session and oversees the collection of the data and analyzes it. For example, it has been proposed in U.S. Pat. No. 6,221,011 and in EP patent application No. EP 1 057 448 A1 that a wide variety of patient data be automatically collected from an IMD in a patient, transmitted over an available network to a remote center 60, and maintained in a patient care record in a centralized database at the center 60. Baseline and updated patient data are maintained in the patient care record by a database server.

As patient population, medical knowledge, and IMD technology expand exponentially, costs also increase such that considerable efforts are brought to bear to make the provision of health care far more efficient and cost effective. A wide variety of initiatives have been undertaken to control costs. Substantial increases in productivity and quality have been associated with the computerization of the work place and the proliferation of information technologies that involve transmission of information between computers leading to a lowering of costs in many industries. Multiple types or combination of network architectures have been put into place, including community access television (CATV) networks, the public switched telephone network (PSTN), the integrated services digital network (ISDN), the Internet, local area networks (LAN), wide area networks (WAN), wireless communications networks, asynchronous transfer mode (ATM) networks, etc, to facilitate such data transmission.

Figure 2:
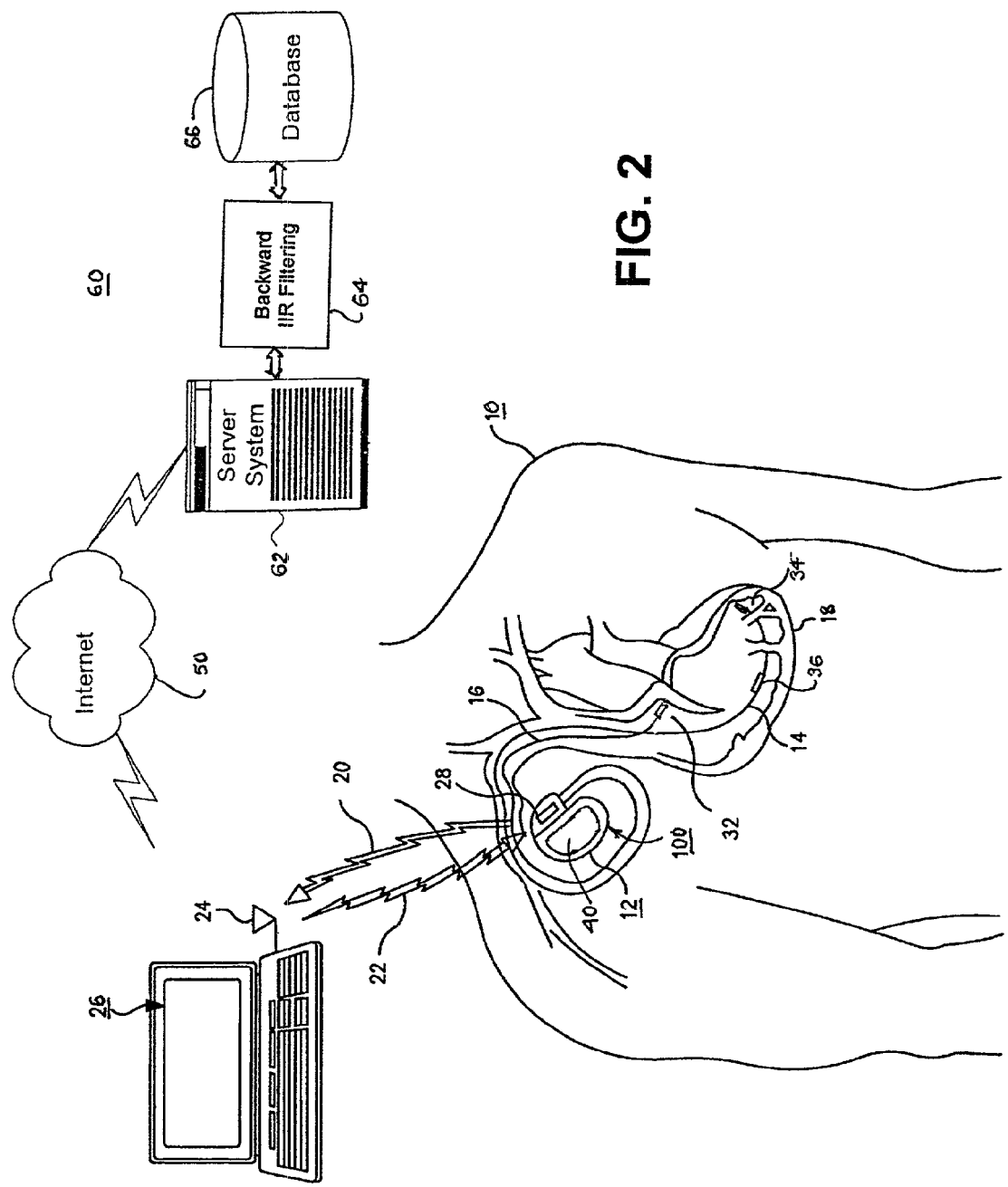
FIG. 2 is a simplified illustration of an exemplary IMD and EMD, optionally involving the remote patient management center.

Thus, in FIGS. 1 and 2, the EMD 26 is optionally in communication with a remote data processing center 60 by way of any of the above-described data transmission modes, e.g., the hardware and software enabling communications over the Internet 50. The remote data processing center 60 shown in FIG. 2 comprises at least a system server 62 and database 64. In accordance with one aspect of the present invention, physiologic signals, e.g., the patient's EGM, is transmitted from the EMD 26 to the remote data processing center 60 where it is stored in the database 66. In this particular embodiment, the data is transmitted through the Internet 50, and EMD 26 simply functions as a data transceiver between the IMD 100 and the remote center 60 and is not capable of programming all of the operating modes and parameters of the IMD 100.

Figure 3:
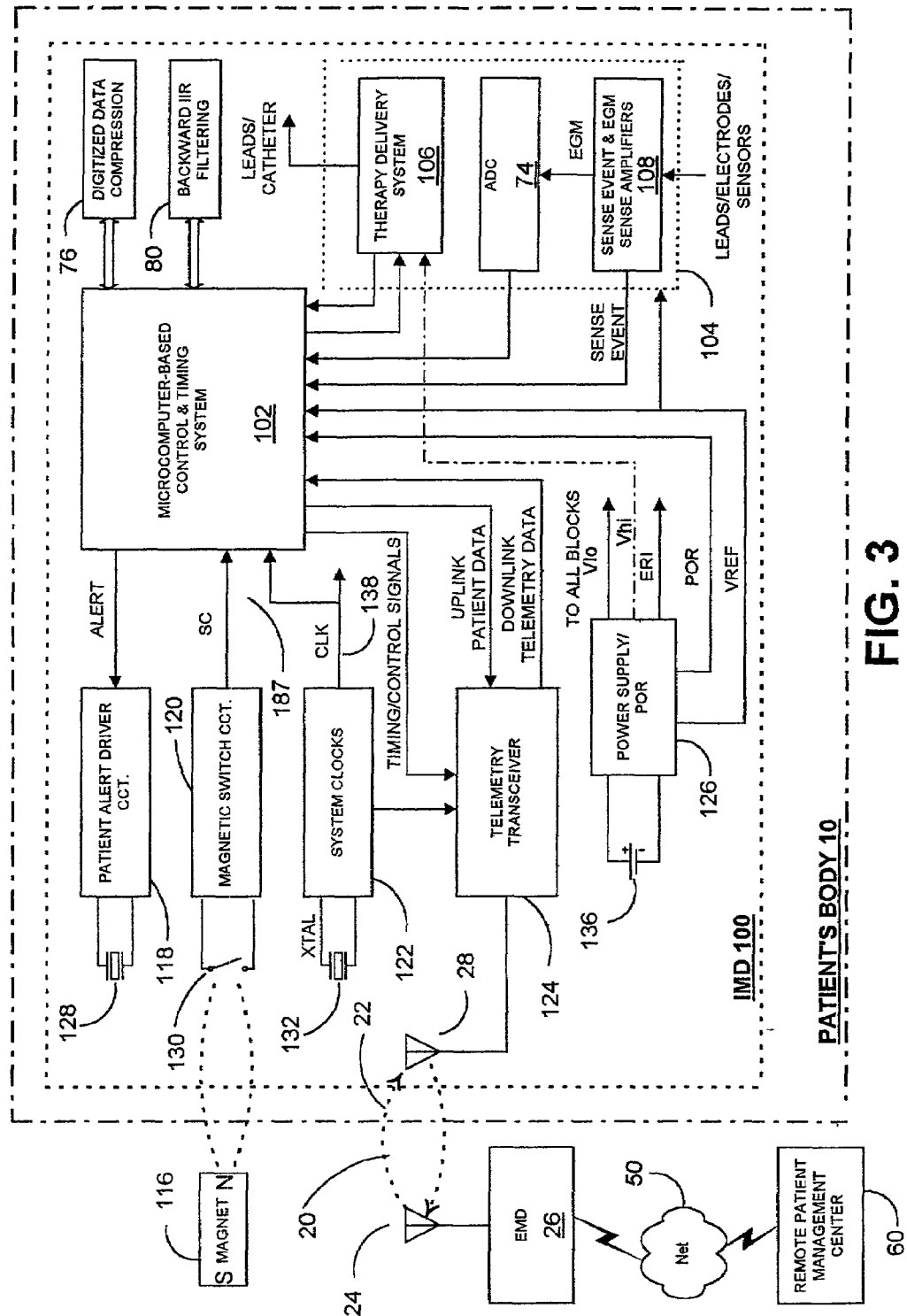
FIG. 3 is a block diagram of a system architecture of an exemplary IMD that incorporates delivery of a therapy and/or physiologic input signal processing in which the signal processing system of the present invention is incorporated.

FIG. 2 illustrates an exemplary cardiac IMD 100, e.g., an ICD, cardiac monitor or cardiac pacemaker implantable pulse generator (IPG) 12 coupled with a ventricular endocardial lead 14 and an atrial endocardial lead 16. FIG. 2 also illustrates bi-directional telemetry communication between an EMD 26 and the cardiac IMD 100 as well as the remote center 60. The IPG 12 contains a battery and an operating system powered by the battery that may employ a microcomputer or a digital state machine for timing and controlling device functions in accordance with a programmed operating mode. An exemplary operating system enclosed within IPG 12 is depicted in FIG. 3 and described further below.

The IPG 12 is implanted in the patient 10 beneath the patient's skin or muscle and is typically oriented to the skin surface. The IPG 12 is electrically coupled to the heart 18 of the patient 10 through pace/sense electrodes 32 and 34 of the endocardial leads 16 and 14, respectively, coupled to the IPG connector in a manner known in the art. The ventricular endocardial lead 14 can also include a physiologic sensor 36, electrically coupled to the IPG connector for sensing a physiologic parameter of the heart, e.g., a pressure sensor for developing a blood pressure signal. The endocardial leads 14 and 16 can also include elongated cardioversion/defibrillation electrodes if the IMD 100 is an ICD. Further or alternative leads can be extended into the coronary sinus of the heart 18 for left heart pacing, sensing and cardioversion purposes as is well known in the art.

When the IPG 12 is provides cardiac pacing and/or monitoring functions, its operating system includes memory registers in RAM for storing a variety of programmed-in operating mode and parameter values that are used by the operating system. The memory registers may also be used for storing patient data compiled from sensed cardiac activity and/or relating to device operating history or sensed physiologic parameters for telemetry out on receipt of downlink transmitted retrieval or interrogation command. The operating system also includes sense amplifiers for detecting cardiac signals, pulse generating output circuits for delivering pacing pulses to at least one heart chamber of the heart 18, and optionally includes patient activity sensors or other physiologic sensors for sensing the need for cardiac output and modulating pacing parameters accordingly in a manner well known in the prior art.

When the IPG 12 is an ICD, it includes one or more high power cardioversion/defibrillation output capacitor, electronic circuitry coupled to the sense amplifiers for detecting and discriminating pathologic and/or non-pathologic arrhythmias from one another and providing other functions, high voltage electronic charging circuitry for charging the output capacitor(s) from a battery voltage to a higher voltage, and electronic switching circuitry for dumping the charge built up on the output capacitor(s) through the cardioversion/defibrillation electrodes. Such a pacing or ICD IPG 12 is described in detail in commonly assigned U.S. Pat. Nos. 5,626,620 or 5,931,857, respectively.

The IPG case can also support a surface electrode 40 for pacing, cardioversion and sensing purposes. The pace/sense electrodes 32 and 34 can comprise a single electrode for unipolar event sensing or for far field EGM sensing in combination with the IPG case surface electrode 40, for unipolar pacing and for delivering cardioversion/defibrillation shocks in combination with cardioversion/defibrillation electrodes on the endocardial leads 14 and 16.

Typically, certain therapy delivery and monitoring operational modes and parameters of the IMD are altered temporarily or chronically in a non-invasive (i.e. non-surgical) manner using downlink telemetry transmission of programming and interrogation commands (herein referred to as "downlink telemetry data") from the external programmer or EMD 26. Moreover, a wide variety of real time and stored physiologic and non-physiologic data (referred to collectively herein as "patient data") is uplink telemetered by the IMD to the EMD 26 in response to a downlink telemetered interrogation command.

The IPG operating system therefore also includes telemetry circuitry and a telemetry antenna 28, which can take the form of a surface mounted antenna or an antenna enclosed within or mounted to the IPG connector. It is desirable to reduce the size of the IPG while increasing its functional capabilities and prolonging battery life to increase longevity. By way of background, the IPG telemetry system and functions with the EMD 26 are first described as follows. For convenience of description, the preferred embodiments are described as follows using RF downlink telemetry (DT) transmissions 22 and uplink telemetry (UT) transmissions 20. The terms "telemeter", "telemetry transmission" and the like are intended to embrace any action and manner of communicating and conveying patient data and downlink telemetry data between the IPG and any EMD or EMD 26 in the UT direction and the DT direction, respectively.

Downlink telemetry data packets and patient data packets are transmitted between the IPG RF telemetry antenna 28 within or on or extending from a surface of the IPG 12 and an external RF telemetry antenna 24 associated with the EMD 26. Preferably, a high frequency carrier signal in the range of 402 to 405 MHz is employed and it is not necessary that the external RF telemetry antenna 24 be located close to the patient's skin overlying the IPG 12. Instead, the external RF telemetry antenna 24 can be located on the case of the external programmer some distance, e.g., about two to five meters, from the patient 10. For example, the EMD 26 and external RF telemetry antenna 24 may be on a stand a few meters or so away from the patient 10 as described, for example, in commonly assigned U.S. Pat. Nos. 5,683,432 and 5,843,139. Moreover, the patient 10 may be active and could be exercising on a treadmill or the like during an uplink telemetry interrogation of real time ECG or physiologic parameters. The EMD 26 may also be designed to universally program existing IPGs 12 that employ the conventional ferrite core, wire coil, RF telemetry antenna of the prior art and therefore also have a conventional programmer RF head and associated software for selective use with such IPGs 12.

In an uplink telemetry transmission 20, the external RF telemetry antenna 24 operates as a telemetry receiver antenna, and the IPG RF telemetry antenna 28 operates as a telemetry transmitter antenna. Conversely, in a downlink telemetry transmission 22, the external RF telemetry antenna 24 operates as a telemetry transmitter antenna, and the IPG RF telemetry antenna 28 operates as a telemetry receiver antenna.

The external RF telemetry antenna 24 within the EMD 26 is coupled to a telemetry transceiver comprising a telemetry transmitter and telemetry receiver, that are coupled to control circuitry and registers operated under the control of a microcomputer and software as described in the above-referenced '139 patent, for example. Similarly, within the IPG 12, the IPG RF telemetry antenna 28 is coupled to a telemetry transceiver comprising a telemetry transmitter and telemetry receiver that are further described below with reference to FIG. 2.

In an uplink telemetry transmission 20, the telemetered patient data may be encoded in any of the telemetry formats. In a particular example described below, the data encoding or modulation is in the form of frequency shift key (FSK) modulation of the carrier frequency, for example. To initiate an uplink telemetry transmission 20, the telemetry transmitter in EMD 26 is enabled in response to a user input to generate an INTERROGATE command in a downlink telemetry transmission 22. The INTERROGATE command is received and demodulated in the receiver and applied to an input of the IMD central processing unit (CPU), e.g. a microcomputer (not shown). The IMD microcomputer responds by forwarding the requested patient data to the transmitter that generates the encoded uplink telemetry transmission 20.

The uplink and downlink telemetry transmissions 20 and 22 follow a telemetry protocol that formulates, transmits and demodulates downlink telemetry data packets and patient data packets each comprising a bit stream of FSK modulated data bits. The data packets are formulated of an FSK data bit stream with a preamble, data and error checking data bits. A carrier frequency centered in a 300 kHz band between 402 MHz and 405 MHz is modulated in frequency or frequency shifted up representing a data bit "1" or shifted down to represent the data bit "0". Each uplink and downlink telemetry transmission 20 and 22 takes place during a respective uplink telemetry transmission time period and downlink telemetry transmission time period.

FIG. 3 depicts a system architecture of an exemplary IMD 100 implanted into a patient's body 10 that provides delivery of a therapy and/or physiologic input signal processing. The typical IMD 100 has a system architecture that is constructed about a microcomputer-based control and timing system 102 that varies in sophistication and complexity depending upon the type and functional features incorporated therein. The functions of microcomputer-based IMD control and timing system 102 are controlled by firmware and programmed software algorithms stored in RAM and ROM including PROM and EEPROM and are carried out using a CPU, ALU, etc., of a typical microprocessor core architecture. The microcomputer-based IMD control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of IMD 100 can be accomplished with dedicated circuit hardware or state machine logic rather than a programmed micro-computer.

The IMD 100 also typically includes patient interface circuitry 104 for receiving signals from sensors or electrodes located at specific sites of a patient's body 10 and/or delivering a therapy to a site of the patient's body 10. The typical patient interface circuitry 104 therefore comprises a therapy delivery system 106 and a physiologic input signal processing circuit 108 or simply one or the other.

The therapy delivery system 106 can be configured to deliver electrical stimulation to the body, e.g., cardioversion/defibrillation shocks and/or cardiac pacing pulses delivered to the heart, or other electrical stimulation delivered to the brain, other organs, selected nerves, the spinal column, the cochlea, or muscle groups, including skeletal muscle wrapped about the heart. Or the therapy delivery system 106 can be configured as a drug pump delivering drugs into organs for therapeutic treatment or into the spinal column for pain relief. Or therapy delivery system 106 can be configured to operate an implantable heart assist device or pump implanted in patients awaiting a heart transplant operation.

It will be understood that most of these therapy delivery IMDs also have a physiologic input signal processing circuit 108 that processes physiologic signals that are used to trigger or modulate therapy delivery and are stored as physiologic signal data for later retrieval as described above. The physiologic input signal processing circuit 108 is coupled to electrical signal sense electrodes and/or physiologic sensors on or in the housing of the IMD 100 or situated at sites distanced from the IMD housing, typically in distal portions of elongated leads. The sensors or electrodes located outside the housing are coupled by conductors to feedthrough pins of feedthroughs extending through the housing wall. Certain physiologic sensors or sense electrodes can be mounted to a connector assembly so that the conductors are quite short. Typically, however, the conductors include the elongated conductors of leads extending to the remotely situated physiologic sensors and sense electrodes.

The IMD 100 can comprise an implantable cardiac monitor without a therapy delivery system 106, e.g., an implantable EGM monitor for recording the cardiac electrogram from electrodes remote from the heart as disclosed in commonly assigned U.S. Pat. No. 5,331,966 and PCT publication WO 98/02209. Or the IMD 100 can comprise an implantable hemodynamic monitor (IHM) for recording cardiac electrogram and other physiologic sensor derived signals, e.g., one or more of blood pressure, blood gases, temperature, electrical impedance of the heart and/or chest, and patient activity. The Medtronic® REVEAL® Insertable Loop Recorder having spaced housing EGM electrodes is an example of the former, and the Medtronic® CHRONICLE® IHM coupled with a capacitive pressure and temperature sensing lead and EGM sense electrodes of the type described in commonly assigned U.S. Pat. No. 5,564,434 is an example of the latter.

In accordance with the present invention, the interface circuitry 104 depicts the application of the EGM signal developed by at least one EGM sense amplifier in sense amplifiers block 108 to the ADC 74. The digitized data bit stream 76 is compressed employing a compression algorithm 76, and blocks of the compressed data are subjected to reverse order IIR filtering using backward IIR filter algorithm 80. Or, blocks of the digitized data bit streams can be subjected to reverse IIR filtering using backward IIR filter algorithm 80 without compression.

These are merely exemplary configurations of IMD 100, therapy delivery system 106, and physiologic input signal processing circuit 108 for therapy delivery and/or monitoring. In all cases, the micro-computer-based control and timing system 102 governs all operating functions employing an appropriate, programmable operating algorithm. FIG. 3 also depicts other typical components common to an IMD 100 in any of these therapy delivery and/or monitoring configurations.

All current IMDs rely upon a source of electrical energy to power the IMD operating system including the circuitry of IMD 100 and to power any electromechanical devices, e.g., valves, pumps, etc. of a substance delivery IMD, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106. Not all of the conventional interconnections of these voltages and signals are shown in FIG. 3.

In addition, in certain IMDs, an audible patient alert warning or message is generated by a transducer 128 when driven by a patient alert driver 118 to advise of device operations, battery power level or a monitored patient condition. In ICDs, the patient may be warned of the detection of a malignant tachyarrhythmia and the imminent delivery of a cardioversion/defibrillation shock to enable the patient to assume a resting position prior to delivery.

Virtually all current electronic IMD circuitry employs clocked CMOS digital logic ICs that require a clock signal CLK provided by a piezoelectric crystal 132 and system clock 122 coupled thereto. In FIG. 3, each CLK signal generated by system clock 122 is routed to all applicable clocked logic via a clock tree 138. The system clock 122 provides one or more fixed frequency CLK signal that is independent of the battery voltage over an operating battery voltage range for system timing and control functions and in formatting uplink telemetry signal transmissions in the telemetry I/O circuit 124.

In the IMD 100, the uplink and downlink telemetry capabilities are provided to enable communication with either a remotely located external medical device or a more proximal medical device on the patient's body or another IMD in the patient's body as described above with respect to FIGS. 1 and 2.

The RAM registers may be used for storing the patient data comprising physiologic patient data compiled from sensed cardiac activity or sensed physiologic parameters and non-physiologic patient data relating to device operating history for uplink telemetry transmission on receipt of a retrieval or interrogation instruction via a downlink telemetry transmission. The criteria for triggering such patient data storage can also be programmed in via downlink telemetry transmitted instructions and parameter values. The physiologic data storage is either triggered on a periodic basis or by detection logic within the physiologic input signal processing circuit 108 upon satisfaction of certain programmed-in event detection criteria. In some cases, the IMD 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted IMD 100 to close switch 130 and prompt the control and timing system to deliver a therapy and/or store physiologic episode data when the patient experiences certain symptoms, e.g. ischemia. In either case, event related data, e.g., the date and time, may be stored along with the stored periodically collected or patient initiated physiologic data for uplink telemetry in a later initiated telemetry session.

In addition, real-time generated physiologic patient data can be transmitted by uplink RF telemetry from the IMD 100 to the external programmer or other remote medical device 26 in response to a downlink telemetered interrogation command. The real-time physiologic data typically includes real time sampled signal levels, e.g., the intracardiac EGM as described above and sensor output signals.

The non-physiologic patient data that can be transmitted by uplink RF telemetry from the IMD 100 to the external programmer or other remote medical device 26 includes currently programmed device operating modes and parameter values, battery condition, device ID, patient ID, implantation dates, device programming history, real time event markers, and the like. In the context of implantable pacemakers and ICDs, such non-physiologic patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies.

The embodiments of the signal measuring system for IMD described above are illustrative of the principles of the present invention and are not intended to limit the invention to the particular embodiments described. For example, in light of the present disclosure, those skilled in the art can device an embodiment of the present invention included within an IMD for filtering high-frequency non-physiologic signals. Accordingly, while the preferred embodiment of the invention has been illustrated and described, it will be appreciated that various changes can be made therein without departing from the spirit and scope of the invention.

CONCLUSION

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of IMDs that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

The invention claimed is:

1. A method for use by an Implantable Medical Device (IMD) of filtering an analog cardiac electrogram (EGM) signal having a predetermined frequency bandwidth, the method comprising:

obtaining an analog cardiac electrogram (EGM) signal from an implantable sensor coupled to the IMD;

filtering the EGM signal with a high pass filter (HPF) having a cut-of frequency within a predetermined frequency bandwidth, and wherein a low-frequency band portion of the predetermined frequency bandwidth is attenuated in the filtered EGM signal;

sampling and digitizing the filtered EGM signal as a digital data set in a time order and optionally, generating a compressed digital data set having at least a 2:1 data compression factor;

filtering one of said digital data set or said compressed data set in reverse time order employing a digital Infinite Impulse Response (IIR) filter having characteristics substantially matching the cut-off frequency and filter characteristics of the HPF to substantially remove distortions of the filtered analog EGM signal introduced by the HPF; and analyzing a reconstituted EGM to determine whether cardiac ischemia is present.

2. The method of claim 1, wherein the method is implemented using programmed instructions.

3. The method of claim 2, wherein the programmed instructions are executed on a processing circuit included within the IMD.

4. The method of claim 2, wherein the programmed instructions are executed on a processing circuit located external to the IMD.

5. The method of claim 1, wherein the EGM signal is generated using at least one of: an endocardial electrode, an epicardial electrode, a subcutaneously implanted electrode, an electrode mechanically coupled to a portion of a housing for the IMD.

6. The method of claim 1, further comprising the step of storing the reverse time order filtered digital data set in a memory structure of the IMD.

7. The method of claim 1, further comprising the steps of:
storing the digital data set in memory of the IMD; and
uplink telemetry transmitting the stored digital data set to an external medical device (EMD); and
wherein the reverse time order filtering step of filtering the digital data set in reverse time order employing a digital IIR filter having characteristics substantially matching the cut-off frequency and filter characteristics of the HPF is conducted by the EMD.

8. Apparatus for use by an Implantable Medical Device (IMD) for filtering a physiological signal having a predetermined frequency bandwidth, the method comprising:
a sensor coupled to the IMD for sensing an analog cardiac electrogram (EGM) signal;
a high pass filter (HPF) for filtering the analog EGM signal, the HPF having a the cut-off frequency within the predetermined frequency bandwidth, wherein a low-band portion of the predetermined frequency bandwidth is attenuated in the filtered analog EGM signal;
means for sampling and digitizing the filtered analog EGM signal as a digital data set In a real time order;
means for compressing the digital data set via a lossy data compression technique wherein said lossy data compression technique comprises a peak preserving compression algorithm providing at least a 2:1 data compression;
a digital Infinite Impulse Response (IIR) filter having characteristics substantially matching the cut-off frequency and filter characteristics of the HPF for reverse time order filtering either said digital data set or said compressed digital data set to substantially remove distortions of the filtered analog physiologic signal introduced by the HPF; and means for comparing an EGM reconstituted from said reverse filtered data to a template to detect ischemia.

9. The apparatus of claim 8, wherein the filtering of the stream of samples with the IIR filter is implemented using programmed instructions.

10. The apparatus of claim 9, wherein the programmed instructions are executed on a processing circuit included within the IMD.

11. The apparatus of claim 9, wherein the programmed instructions are executed on a processing circuit located external to the IMD.

12. The apparatus of claim 8, wherein the EGM signal is generated by at least one of: an endocardial electrode, an epicardial electrode, a subcutaneously implanted electrode, an electrode mechanically coupled to a portion of a housing for the IMD.

13. The apparatus of claim 8, further comprising means for storing the reverse time order filtered digital data set in memory of the IMD.

14. The apparatus of claim 8, further comprising:
means for storing the compressed digital data set in memory of the IMD; and
means for uplink telemetry transmitting the stored compressed digital data set to an external medical device (EMD); and wherein:
the digital IIR filter having characteristics substantially matching the cut-off frequency and filter characteristics of the HPF is within the EMD; and
the EMD further comprises means for receiving the uplink telemetry transmitted compressed digital data set and applying the received compressed digital data set to the digital IIR filter in reverse time order.

15. Apparatus for use by an Implantable Medical Device (IMD) for filtering a physiological signal having a predetermined frequency bandwidth, the method comprising:
a sensor coupled to the IMD for sensing an analog cardiac electrogram (EGM) signal;
a high pass filter (HPF) for filtering the analog EGM signal, the HPF having a the cut-off frequency within the predetermined frequency bandwidth, wherein a low-band portion of the predetermined frequency bandwidth is attenuated in the filtered analog EGM signal;
means for sampling and digitizing the filtered EGM signal as a digital data set in a real time order;
optionally, means for compressing said digital data set;
a digital Infinite Impulse Response (IIR) filter having characteristics substantially matching the cut-off frequency and filter characteristics of the HPF for reverse time order filtering the digital data set, or a compressed data set if said optional means for compressing is included, to substantially remove distortions of the filtered analog EGM signal introduced by the HPF: and
means for comparing an EGM reconstituted from said reverse filtered data to a template to detect ischemia.

16. The apparatus of claim 15, wherein the filtering of the stream of samples with the IIR filter is implemented using programmed instructions.

17. The apparatus of claim 16, wherein the programmed instructions are executed on a processing circuit included within the IMD.

18. The apparatus of claim 16, wherein the programmed instructions are executed on a processing circuit located external to the IMD.

19. The apparatus of claim 15, wherein the physiologic signal is generated by at least one of: an endocardial electrode, an epicardial electrode, a subcutaneously implanted electrode, an electrode mechanically coupled to a portion of a housing for the IMD.

20. The apparatus of claim 15, further comprising means for storing the reverse time order filtered digital data set in memory of the IMD.

21. The apparatus of claim 15, further comprising:
means for storing the digital data set in memory of the IMD; and
means for uplink telemetry transmitting the stored digital data set to an external medical device (EMD); and wherein:

the digital IIR filter having characteristics substantially matching the cut-off frequency and filter characteristics of the HPF is within the EMD; and the FMD further comprises means for receiving the uplink telemetry transmitted digital data set and applying the received digital data set to the digital IIR filter in reverse time order.

* * * * *

UNITED STATES PATENT AND TRADEMARK OFFICE
CERTIFICATE OF CORRECTION

PATENT NO. : 7,120,484 B2
APPLICATION NO. : 10/045722
DATED : October 10, 2006
INVENTOR(S) : Lu et al.

Page 1 of 1

It is certified that error appears in the above-identified patent and that said Letters Patent is hereby corrected as shown below:

Column 15, line 2 please change "a cut-of" to --a cut-off--.

Signed and Sealed this

Twenty-third Day of October, 2007

JON W. DUDAS
*Director of the United States Patent and Trademark Office*